US012544115B2

(12) United States Patent
Gallant et al.

(10) Patent No.: US 12,544,115 B2
(45) Date of Patent: Feb. 10, 2026

(54) SPINOUS PROCESS CLAMP

(71) Applicant: Medivis, Inc., New York, NY (US)

(72) Inventors: Jesse Harrison Gallant, New York, NY (US); Christopher Morley, New York, NY (US); Osamah Choudhry, New York, NY (US)

(73) Assignee: Medivis, Inc., New York, NY (US)

( * ) Notice: Subject to any disclaimer, the term of this patent is extended or adjusted under 35 U.S.C. 154(b) by 218 days.

(21) Appl. No.: 18/135,663

(22) Filed: Apr. 17, 2023

(65) Prior Publication Data

US 2024/0341820 A1 Oct. 17, 2024

(51) Int. Cl.
*A61B 17/70* (2006.01)

(52) U.S. Cl.
CPC ................................ *A61B 17/7047* (2013.01)

(58) Field of Classification Search
CPC ....... A61B 17/7047; B25B 5/10; B25B 5/102; B25B 5/104; B25B 5/106; B25B 5/108
See application file for complete search history.

(56) References Cited

U.S. PATENT DOCUMENTS 7,993,353 B2 * 8/2011 Roßner .................. A61B 90/39 606/130
2004/0068263 A1 * 4/2004 Chouinard ............. A61B 90/10 606/86 R
2008/0221625 A1 * 9/2008 Hufner ............... A61B 17/1757 606/151
2009/0024127 A1 * 1/2009 Lechner ................. A61B 90/39 606/53
2009/0062869 A1 * 3/2009 Claverie ............ A61B 17/8866 606/151
2012/0221059 A1 * 8/2012 Mollman ........... A61B 17/7074 606/279
2018/0092667 A1 * 4/2018 Heigl ................. A61B 17/7047
2022/0257334 A1 * 8/2022 Guthart .................. A61B 90/39

FOREIGN PATENT DOCUMENTS

DE 2936474 A1 * 3/1981 ......... A61B 17/2812

* cited by examiner

*Primary Examiner* — Nicholas W Woodall
(74) *Attorney, Agent, or Firm* — Cognition IP, P.C.; Edward Steakley; Justin White

(57) ABSTRACT

A spinous process clamp can include opposing arms, opposing gripping components, an adjustable spacing arrangement, and a coupling component. Each arm can have a top distal end, a midsection, and a bottom distal end. Each gripping component can be located proximate the bottom distal end of an arm and can be configured to grip a side of a spinous process. The arms can be pivotally coupled about their midsections to adjust the distance between the gripping components. The adjustable spacing arrangement can be coupled to the arms proximate their top distal ends and can be configured to adjust and maintain a pivoted position of the arms. The coupling component can be coupled to the top distal end of and arm and can be configured to rotationally couple the spinous process clamp to a separate surgical component, which can be a surgical fiducial marker positioner.

21 Claims, 14 Drawing Sheets

SPINOUS PROCESS CLAMP

CROSS-REFERENCE TO RELATED APPLICATION

This application is related to commonly owned U.S. Patent Application No. 18/135,674 filed on this same date of Apr. 17, 2023 and entitled "SURGICAL FIDUCIAL MARKER POSITIONER," which application is hereby incorporated by reference in its entirety.

TECHNICAL FIELD

The present disclosure relates generally to medical devices, and more particularly to surgical tools and devices used during medical surgeries and procedures.

BACKGROUND

Planning and navigation are necessary for many medical procedures, and surgical teams typically have a plan based on medical imagery before ever entering an operating room. Conventional medical imaging systems such as X-ray, MRI, CT, and others have limitations regarding two-dimensional and three-dimensional images, however, and surgeons often need to consider numerous image views and slices to plan surgical procedures. Recent medical advances leverage these applications of medical imagery and surgical plans by using a computer-aided augmented reality environment, which can allow for the tracking of patients and physical instruments during surgical procedures by using fiducial markers and tracking components.

Unfortunately, conventional tracking systems are often limited in their ability to accurately generate, render, and apply virtual interactions in an augmented reality environment based on the orientations and positions of physical instruments with respect to those of physical landmarks identified on a patient body, particularly when things move during surgery. Unstable or unreliable positioning of fiducial markers can play a role in these issues. Limited or inaccurate tracking can then affect the overall performance of such systems during surgical procedures, and the need for accuracy in this regard can lead to overly cumbersome or complex attachment devices and systems.

While traditional ways of virtually tracking items during surgery have worked well in the past, improvements are always helpful. In particular, what is desired are medical systems and devices that facilitate the stable and reliable positioning of fiducial markers during surgery in a simple and streamlined manner.

SUMMARY

It is an advantage of the present disclosure to provide medical systems and devices that facilitate the stable and reliable positioning of fiducial markers during surgery in a simple and streamlined manner. The disclosed features, apparatuses, systems, and methods relate to clamps that can be used to affix surgical devices and equipment to patients during surgeries and other medical procedures. In particular, the disclosed systems and methods can involve spinous process clamps that can be clamped onto a spinous process of a patient and that are arranged to be coupled to one or more other surgical devices or items, such as a fiducial marker positioner.

In various embodiments of the present disclosure, a spinous process clamp can include a first arm, a first gripping component, a second arm, a second gripping component, an adjustable spacing arrangement, and a coupling component. The first arm can have a top distal end, a midsection, and a bottom distal end. The first gripping component can be located proximate the bottom distal end of the first arm and can be configured to grip a side of a spinous process of a patient. The second arm can be positioned opposite the first arm and can similarly have a top distal end, a midsection, and a bottom distal end. The midsection of the second arm can be pivotally coupled to the midsection of the first arm. The second gripping component can be located proximate the bottom distal end of the second arm and can be configured to grip a side of the spinous process opposite the side gripped by the first gripping component, wherein pivoting the first and second arms with respect to each other adjusts a distance between the first and second gripping components. The adjustable spacing arrangement can be coupled to the first arm proximate its top distal end and to the second arm proximate its top distal end, and this adjustable spacing arrangement can be configured to maintain a pivoted position of the first and second arms with respect to each other such that adjustment of the adjustable spacing arrangement results in pivoting the first and second arms with respect to each other. The coupling component can be coupled to the first arm proximate its top distal end and can be configured to couple the spinous process clamp to a separate surgical component.

In various detailed embodiments, the coupling component can be configured to rotationally couple the spinous process clamp to a separate surgical component about at least one axis of rotation. The coupling component can be also configured to facilitate at least ten different discrete rotational positions of the separate surgical component with respect to the spinous process clamp. The separate surgical component can be a surgical fiducial marker positioner and fiducial markers of the surgical fiducial marker positioner can include infrared reflective balls. In some arrangements, the adjustable spacing arrangement can include a threaded bar and a thumbwheel located on the threaded bar. Rotation of the thumbwheel in a forward direction can cause the top distal ends of both arms to move toward the thumbwheel equally and rotation of the thumbwheel in a reverse direction can cause the top distal ends of both arms to move away from the thumbwheel equally. The threaded bar can include a left-hand thread on one side of the threaded bar and a right-hand thread on the opposite side of the threaded bar. The adjustable spacing arrangement can further include a first receiving bearing at the first arm and a second receiving bearing at the second arm, and each of the first and second receiving bearings can include a threaded interior passage configured to receive the threaded bar. Each of the receiving bearings can also be located within and configured to rotate relative to a top distal end of its respective arm. In various arrangements, each of the first and second gripping components can define an outer perimeter having a plurality of gripping teeth distributed thereabout. Each of the gripping components can further include at least one gripping tooth located within this outer perimeter. Also, at least the first gripping component can be pivotally coupled to the bottom distal end of the first arm.

In further embodiments of the present disclosure, various methods of using a spinous process clamp are provided. Pertinent process steps can include opening a distance between gripping components of a spinous process clamp, placing the gripping components around a spinous process of a patient, and closing the distance between the gripping components until the gripping components grip the spinous process and affix the spinous process clamp in place relative to the patient.

In various detailed embodiments, the spinous process clamp can include a first arm, a first gripping component, a second arm, a second gripping component, an adjustable spacing arrangement, and a clamp coupling component, all of which can include some or all of the various features set forth above for spinous process clamps. Additional process steps can include coupling the spinous process clamp to a surgical fiducial marker positioner, rotating the surgical fiducial marker positioner with respect to the spinous process clamp while the spinous process clamp is coupled to the surgical fiducial marker positioner and the spinous process clamp is affixed in place relative to the patient, affixing the rotational position of the surgical fiducial marker positioner relative to the spinous process clamp.

In still further embodiments of the present disclosure, a surgical fiducial marker system can include a spinous process clamp and a surgical fiducial marker positioner. The spinous process clamp can be configured to grip a spinous process of a patient, while the surgical fiducial marker positioner can be rotationally coupled to the spinous process clamp. The surgical fiducial marker positioner can be configured to position a plurality of surgical fiducial markers into a fixed arrangement relative to the patient while the spinous process clamp grips the spinous process of the patient.

In various detailed embodiments, the spinous process clamp can include a first arm, a first gripping component, a second arm, a second gripping component, an adjustable spacing arrangement, and a clamp coupling component, all of which can include some or all of the various features set forth above for spinous process clamps. In some arrangements, the clamp coupling component can be configured to facilitate at least ten different discrete rotational positions of the surgical fiducial marker positioner with respect to the spinous process clamp. Also, the clamp coupling component can rotationally mate with a corresponding positioner coupling component on the surgical fiducial marker positioner.

Other apparatuses, methods, features, and advantages of the disclosure will be or will become apparent to one with skill in the art upon examination of the following figures and detailed description. It is intended that all such additional apparatuses, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures, arrangements, and methods of use for spinous process clamps. These drawings in no way limit any changes in form and detail that may be made to the disclosure by one skilled in the art without departing from the spirit and scope of the disclosure.

DETAILED DESCRIPTION

Figure 1A:
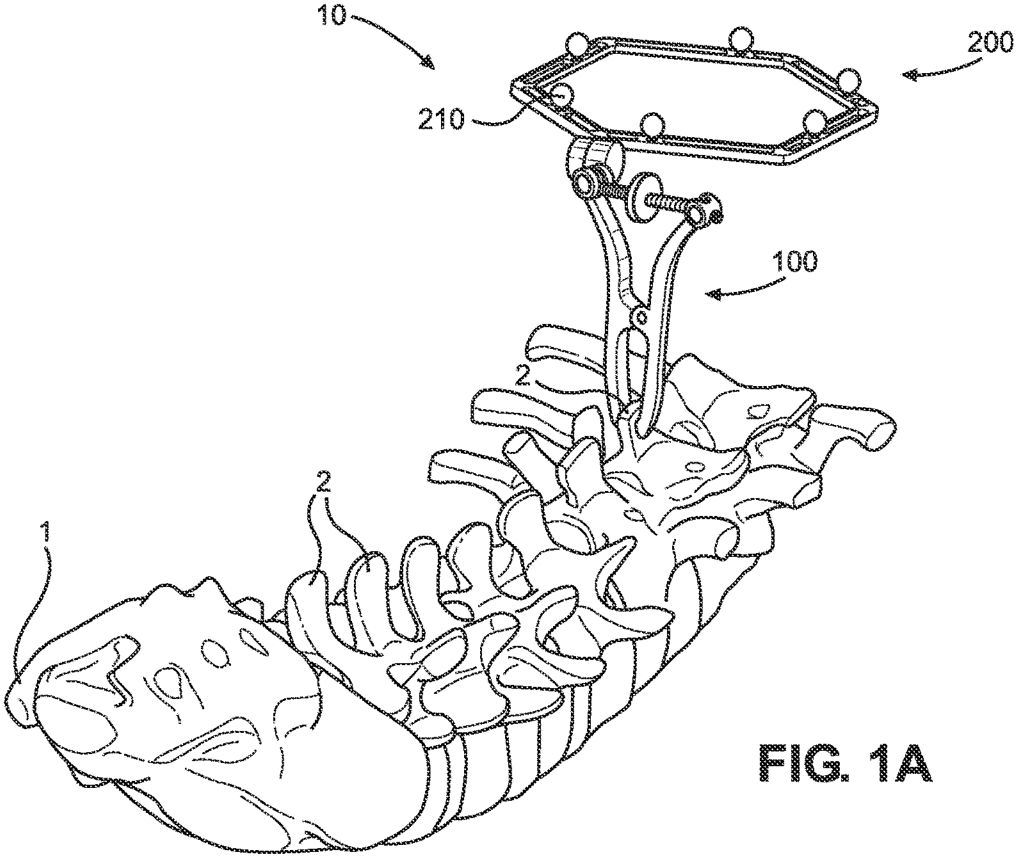
FIG. 1A illustrates in front perspective view an example surgical fiducial marker system having a spinous process clamp according to one embodiment of the present disclosure.

Exemplary applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details provided herein. In some instances, well known process steps have not been described in detail in order to avoid unnecessarily obscuring the present disclosure. Other applications are possible, such that the following examples should not be taken as limiting. In the following detailed description, references are made to the accompanying drawings, which form a part of the description and in which are shown, by way of illustration, specific embodiments of the present disclosure. Although these embodiments are described in sufficient detail to enable one skilled in the art to practice the disclosure, it is understood that these examples are not limiting, such that other embodiments may be used, and changes may be made without departing from the spirit and scope of the disclosure.

As is generally well known, modern surgical plans and procedures are sometimes facilitated by using a computer-aided augmented reality environment. Surgical fiducial markers can be used for tracking of patients and physical instruments during surgical procedures in overall systems that can also include specialized lighting arrangements, cameras, and computing systems. Attachment devices are often used to affix the surgical fiducial markers in place relative to the patient, and unstable or unreliable positioning of these markers can result in the reduced effectiveness of the overall computer-aided augmented reality environment. The disclosed surgical attachment devices are specifically designed to facilitate the stable and reliable positioning of fiducial markers during surgery in a simple and streamlined manner.

The present disclosure relates in various embodiments to features, apparatuses, systems, and methods of use for surgical attachment devices, and in particular spinous process clamps. This can generally involve clamps or other suitable attachment devices that are configured to attach to patient bodies during surgical processes while also providing for the ability to be coupled to other surgical devices or equipment. In specific arrangements this can involve a spinous process clamp configured to clamp or attach to a spinous process while also having a surgical fiducial marker positioner attached thereto.

In various embodiments of the present disclosure, novel spinous process clamps can include gripping components located at or proximate the ends of opposing arms and configured to move with respect to the opposing arms. The opposing arms can be configured to move such that the gripping components can be closed to clamp the spinous process clamp onto a spinous process and can be opened to remove the spinous process clamp from the spinous process. An adjustable spacing arrangement can be coupled to both arms and can be configured to enable controlled arm movements that open and close the distance between the gripping components. A coupling component coupled to at least one arm can be configured for coupling the spinous process clamp to a separate surgical component, such as a surgical fiducial marker positioner. In some arrangements, the adjustable spacing arrangement and the coupling component can be located at or proximate arm ends opposite the ends with the gripping components.

Although various embodiments disclosed herein discuss the use of a spinous process clamp in conjunction with a surgical fiducial marker positioner as part of an overall surgical fiducial marker system, it will be readily appreciated that the disclosed features, apparatuses, systems, and methods can also be used in conjunction with other devices and equipment that can leverage the advantages of such a clamp. While the disclosed spinous process clamps are contemplated for use involving clamping to spinous processes during a surgical procedure, it is specifically contemplated that other clamped objects and applications may also be applied. For example, the disclosed spinous process clamps can be used to clamp to other bones or body parts for surgical and non-surgical uses, such as during examination and testing procedures. Further, other devices and equipment that can be coupled to the disclosed spinous process clamps can include lighting arrangements, sensing devices, or other desired equipment. Other applications, arrangements, and extrapolations beyond the illustrated embodiments are also contemplated.

Figure 1B:
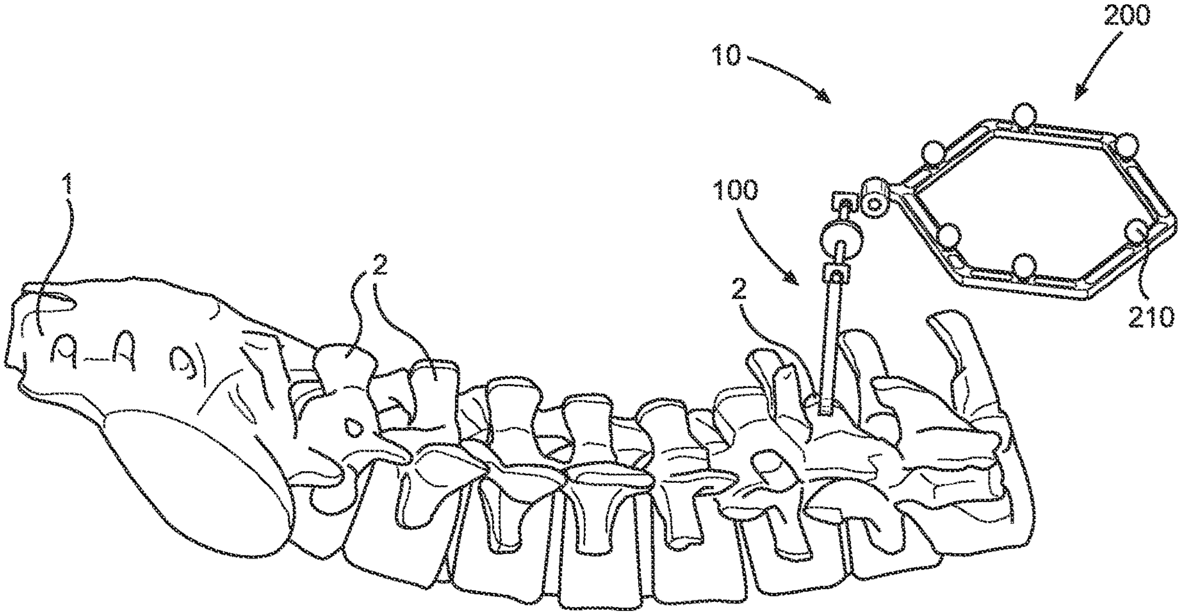
FIG. 1B illustrates in side perspective view the surgical fiducial marker system of FIG. 1A according to one embodiment of the present disclosure.

Referring first to FIGS. 1A and 1B, an example surgical fiducial marker system having a spinous process clamp is illustrated in front perspective and side perspective views respectively. Surgical fiducial marker system 10 can generally include a spinous process clamp 100 and a surgical fiducial marker positioner 200. Spinous process clamp 100 can be clamped to one of various spinous processes 2 along the spine 1 of a patient. Surgical fiducial marker positioner 200 can be coupled to spinous process clamp 100 and can be configured to position multiple surgical fiducial markers 210 with respect to the patent spine 1.

Figure 2A:
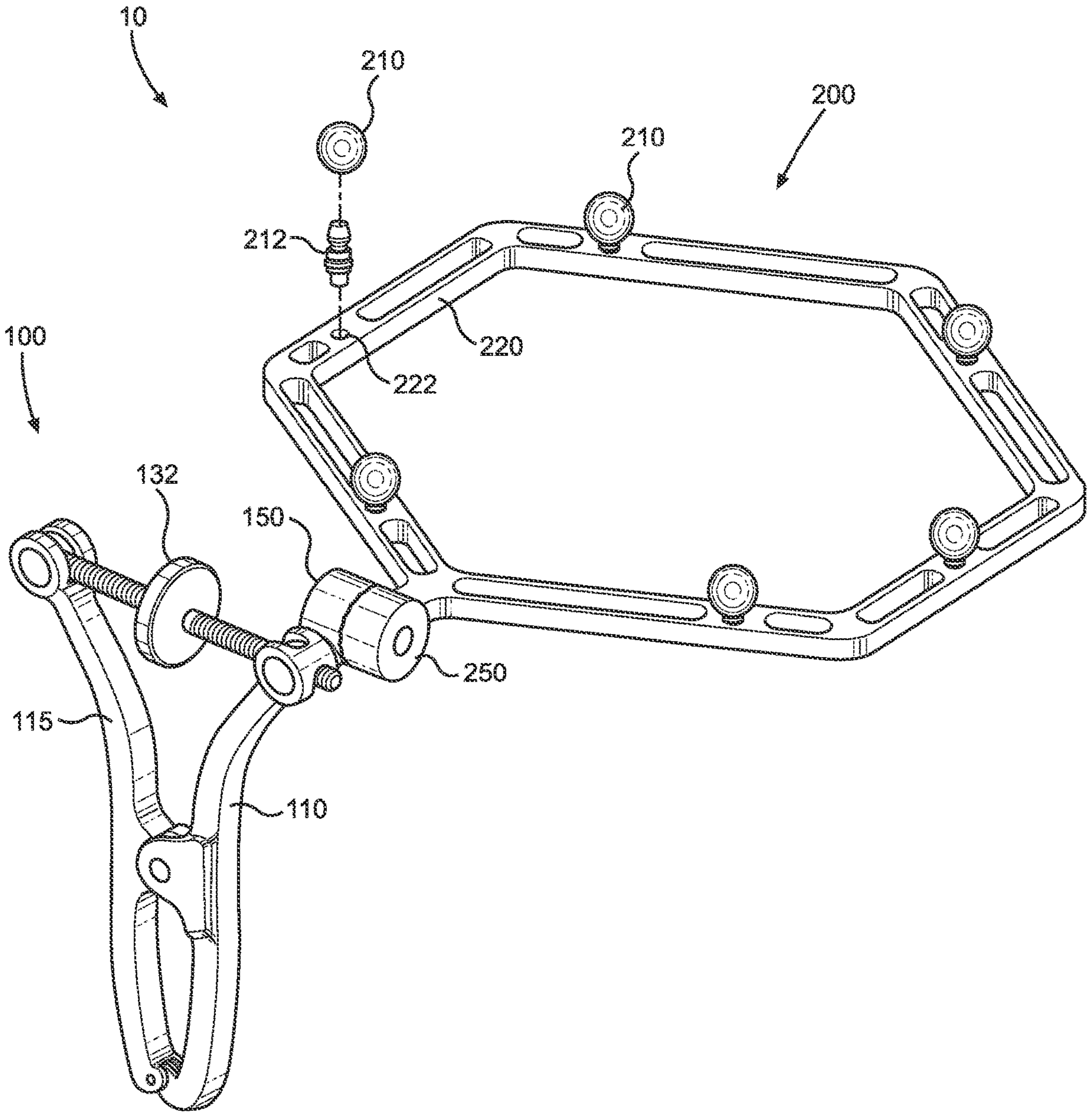
FIG. 2A illustrates in front perspective view an example surgical fiducial marker system having a spinous process clamp according to one embodiment of the present disclosure.

Continuing with FIG. 2A, an example surgical fiducial marker system having a spinous process clamp is shown in front perspective view. Again, surgical fiducial marker system 10 can generally include a spinous process clamp 100 and a surgical fiducial marker positioner 200. In various embodiments, spinous process clamp 100 can include a first arm 110, a second arm 115, a thumbwheel 132, and a clamp coupling component 150, among various other components and features set forth in greater detail below. While clamp coupling component 150 is shown as being located proximate the top of first arm 110, it will be readily appreciated that this coupling component can alternatively be located at various other places on spinous process clamp 100, such as proximate the top of second arm 115 for example.

Surgical fiducial marker positioner 200 can be configured to position multiple surgical fiducial markers 210 with respect to a patient and can be coupled to spinous process clamp 100 by way of a positioner coupling component 250 that can be configured to interact with clamp coupling component 150 of the clamp, as detailed below. In various embodiments, surgical fiducial markers 210 can include infrared reflective balls or other retroreflective spheres, infrared-emitting diodes, or other items suitable for use with surgical optical tracking systems. Each surgical fiducial marker 210 can be coupled to an arm segment 220 of surgical fiducial marker positioner 200 using a threaded coupler 212 that can be inserted into an opening of the fiducial marker as well as an opening 222 along the arm segment 220.

As shown in FIG. 2A, surgical fiducial marker positioner 200 can include multiple arm segments 220 arranged into an irregular polygon shape, such as a hexagon. Each arm segment 220 can include an opening 222 for a surgical fiducial marker 210, which can be removably coupled to the opening 222. The locations of openings 222 can form an asymmetrical pattern such that installation of surgical fiducial markers 210 into all of the openings then results in an asymmetrical pattern that will not cause ambiguity or confusion with the optical tracking system reading the locations of the fiducial markers. Although six surgical fiducial markers and six arm segments 220 arranged into a hexagon shape are shown for purposes of illustration, it will be understood that a suitable surgical fiducial marker positioner may also have more or fewer fiducial markers arranged along more or fewer arm segments arranged into other shapes. Such other shapes can include rectangles, pentagons, octagons, for example, among other possible shapes. Further details regarding surgical fiducial marker positioner 200 can be found in related U.S. Patent Application No. 18/135,674 entitled "SURGICAL FIDUCIAL MARKER POSITIONER," which application is again hereby incorporated by reference in its entirety.

Figure 2B:
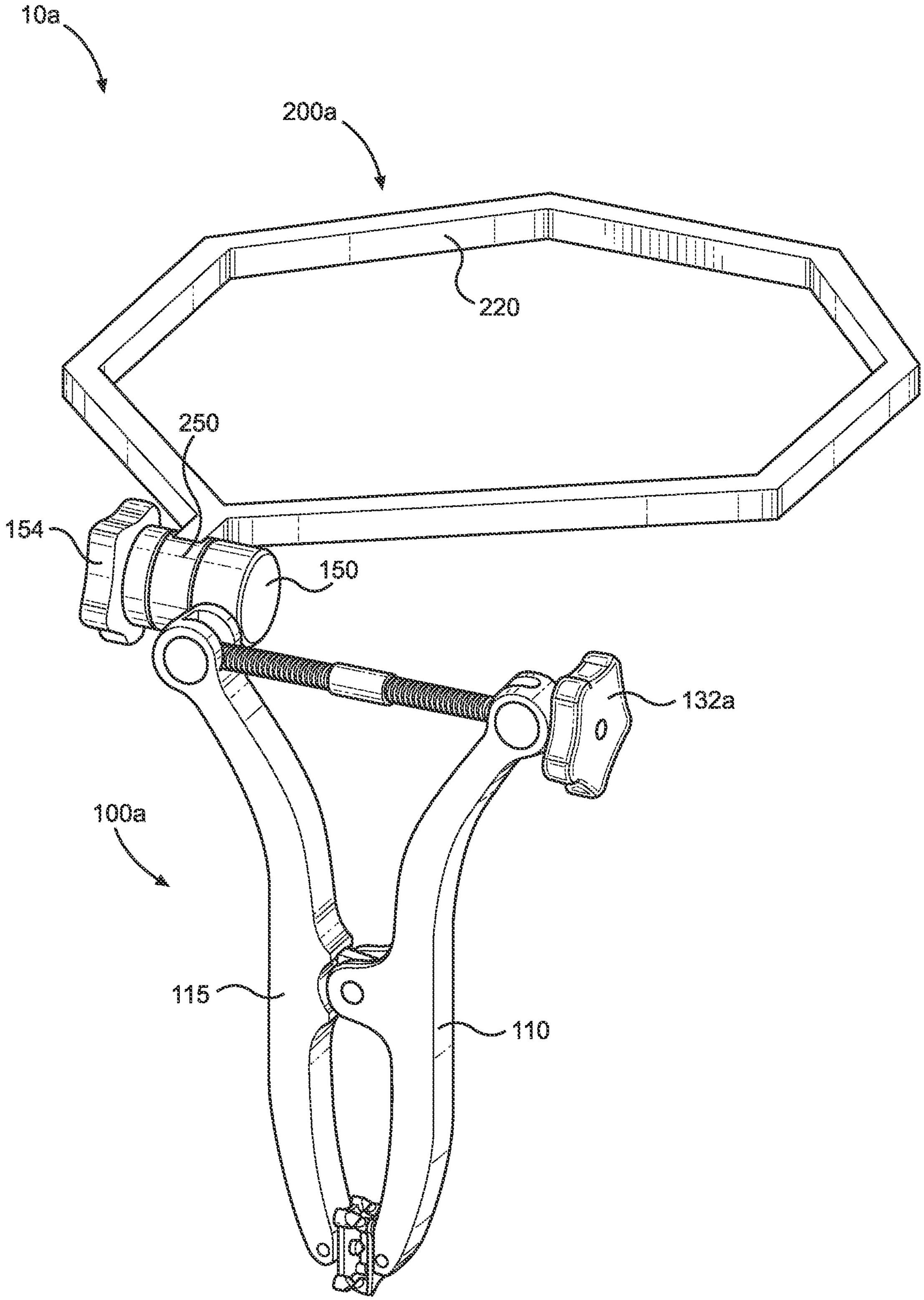
FIG. 2B illustrates in front perspective view an example surgical fiducial marker system with a spinous process clamp according to another embodiment of the present disclosure.

FIG. 2B illustrates in front perspective view an example alternative surgical fiducial marker system with a spinous process clamp. Alternative surgical fiducial marker system 10*a* can be substantially similar to surgical fiducial marker system 10 in FIG. 2A, only with some variations to different components. Alternative fiducial marker system 10*a* can include an alternative spinous process clamp 100*a* and alternative surgical fiducial marker positioner 200*a* that both have minor variations from spinous process clamp 100 and surgical fiducial marker positioner 200. For example, alternative spinous process clamp 100*a* can include thumbwheel 132*a* located outside of first arm 110 and second arm 115 rather than between these arms, and this alternative thumbwheel 132*a* can have multiple nodules forming a star-shape rather than the circular shape of thumbwheel 132 above. Also, clamp coupling component 150 can be located proximate the top of second arm 115, and a thumbwheel and pin arrangement 154 can be used to tighten positioner coupling component 250 against clamp coupling component 150, as noted below. As another example, alternative surgical fiducial marker positioner 200*a* can have seven arm segments 220 rather than the six arm segments 220 shown for surgical fiducial marker positioner 200 in FIG. 2A. Other minor variations in system features are also possible.

Figure 3A:
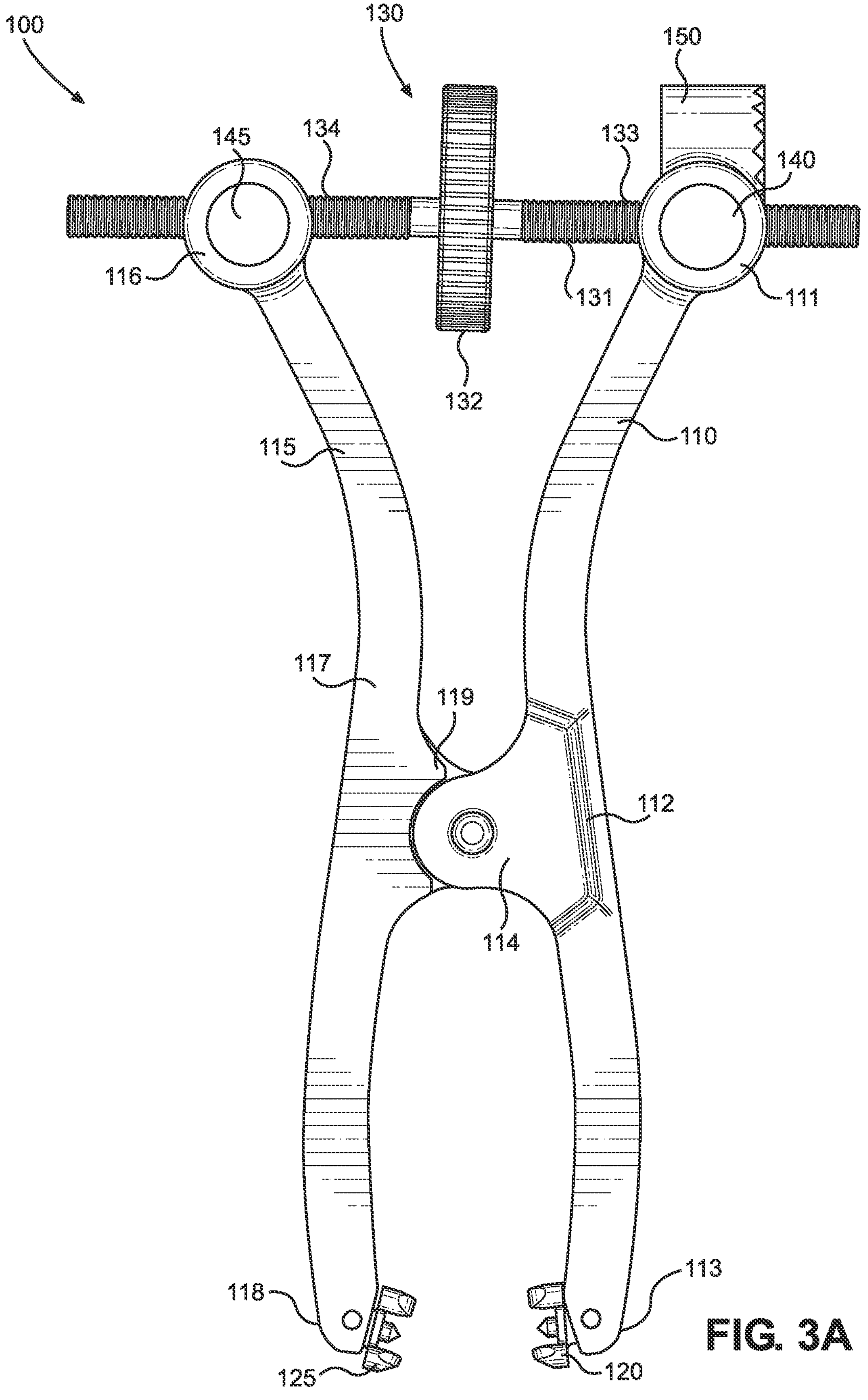
FIG. 3A illustrates in front elevation view an example spinous process clamp at an open position according to one embodiment of the present disclosure.
Figure 3B:
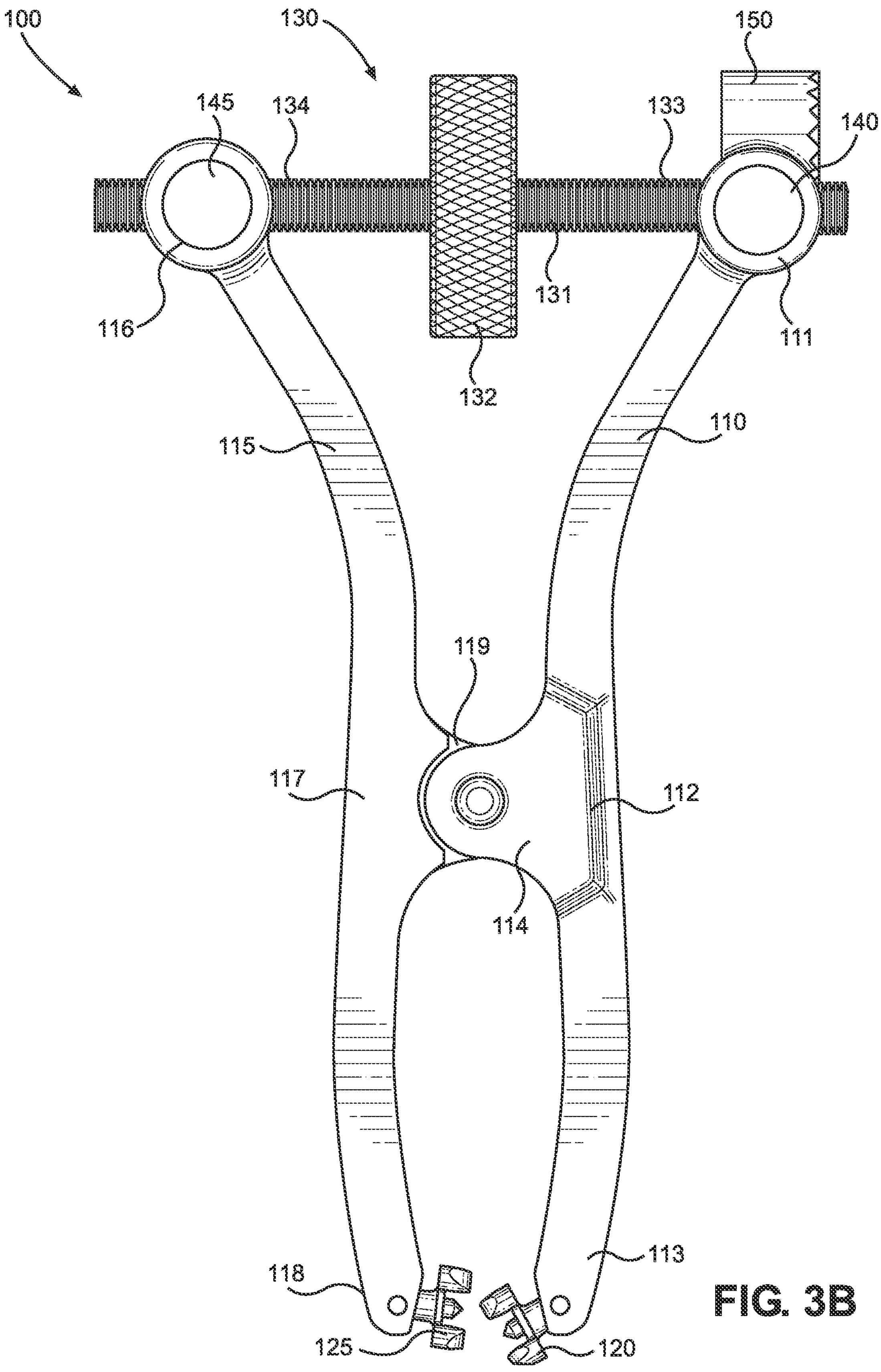
FIG. 3B illustrates in front elevation view the spinous process clamp of FIG. 3A at a closed position according to one embodiment of the present disclosure.

Focusing now on FIGS. 3A and 3B, an example spinous process clamp is shown in front elevation views in open and closed positions respectively. Spinous process clamp 100 can include a first arm 110, a second arm 115, a first gripping component 120, a second gripping component 125, an adjustable spacing arrangement 130 including a first receiving bearing 140 and a second receiving bearing 145, and a clamp coupling component 150, among other possible components and features. First arm 110 can have a top distal end 111, a midsection 112, a bottom distal end 113, and a first pivoting feature 114, while second arm 115 can similarly have a top distal end 116, a midsection 117, a bottom distal end 118, and a second pivoting feature 119. Midsection 117 of second arm 115 can be pivotally coupled to midsection 112 of first arm 110 by way of a pivoting arrangement between first and second pivoting features 114, 119. Clamp coupling component 150 can be coupled to first arm 110 proximate its top distal end 111 and can be configured to couple spinous process clamp 100 to a separate surgical component, such as a surgical fiducial marker positioner 200, as noted above.

First gripping component 120 can be located proximate bottom distal end 113 of first arm 110 and can be configured to grip a side of a spinous process of a patient, while second gripping component 125 can similarly be located proximate bottom distal end 118 of second arm 115 and can be configured to grip a side of the spinous process opposite the side gripped by the first gripping component. Pivoting first and second arms 110, 115 with respect to each other can adjust a distance between first and second gripping components 120, 125. As shown in FIG. 3A, first and second arms 110, 115 of spinous process clamp 100 are pivoted to put the clamp into an "open" position such that first and second gripping components 120, 125 are spaced relatively far apart. Conversely, FIG. 3B depicts first and second arms 110, 115 of spinous process clamp 100 as pivoted to put the clamp into a "closed" position such that first and second gripping components 120, 125 are spaced relatively close together. While specific open and closed positions are shown in FIGS. 3A and 3B, it will be readily appreciated that spinous process clamp 100 can be adjusted to a wide variety of positions having different exact distances between first and second gripping components 120, 125.

The exact spacing or distance between first and second gripping components 120, 125 can be facilitated by adjustable spacing arrangement 130, which can be coupled to first arm 110 proximate top distal end 111 and to second arm 115 proximate top distal end 116. Adjustable spacing arrangement 130 can include threaded bar 131, thumbwheel 132 located proximate the center of the threaded bar, and first and second receiving bearings 140, 145 located on opposite sides of the thumbwheel toward the distal ends of the threaded bar. In some arrangements thumbwheel 132 can be integrally formed with threaded bar 131, while in other arrangements this thumbwheel can be firmly attached to the threaded bar as a separate component. Each of first and second receiving bearings 140 and 145 can be located at and rotatable within top distal ends 111 and 116 respectively. Each of first and second receiving bearings 140 and 145 can also have an internal threaded portion configured to receive respective first and second threaded portions 133, 134 of threaded bar 131 and pass those respective threaded portions therethrough when the threaded bar is rotated, such as by thumbwheel 132.

Adjustable spacing arrangement 130 can be configured to maintain a pivoted position of first and second arms 110, 115 with respect to each other. For example, external threads along first and second threaded portions 133, 134 of threaded bar 131 can engage with internal threads of respective first and second receiving bearings 140, 145 such that these receiving bearings do not slide along the threaded bar, while a tight fit between these receiving bearings and their respective top distal ends 111, 116 of first and second arms 110, 115 prevent relative pivoting or rotational movement of the arms. Rotational adjustment of adjustable spacing arrangement 130 can result in pivoting first and second arms 110, 115 with respect to each other. For example, rotation of thumbwheel 132 in one direction can result in rotation of first and second threaded portions 133, 134 of threaded bar 131, which can in turn result in movement of first and second receiving bearings 140, 145 along their respective threaded portions, which can then result in movement of top distal ends 111, 116 of first and second arms 110, 115.

Thumbwheel 132 can be operated manually, such as by a surgeon, for example, in some embodiments, or can alternatively be automatically controlled by one or more robotic components in some situations. In some arrangements, rotation of thumbwheel 132 in a forward or "clamp opening" direction can result in moving receiving bearings 140, 145 and top distal ends 111, 116 toward the thumbwheel, which can then result in increasing the distance between first and second gripping components 120, 125 due to the pivoting arrangement of first and second arms 110, 115. In such arrangements, rotation of thumbwheel 132 in a reverse or "clamp closing" direction can then result in moving receiving bearings 140, 145 and top distal ends 111, 116 away from the thumbwheel, which can then result in decreasing the distance between first and second gripping components 120, 125 due to arm pivoting.

As noted above, thumbwheel 132 can take alternative forms and can be located at other places along threaded bar 131. FIG. 2B depicts a star-shaped thumbwheel 132*a* having five nodules, for example, and this thumbwheel 132*a* can be located on threaded bar 131 on or at its distal end outside of first arm 110. More or fewer than five nodules of a star-shape are also possible, other alternative thumbwheel shapes are also possible, and the location of the thumbwheel can be on or at the other end of threaded bar 131 or at any other suitable location along the threaded bar. Other mechanisms or features for readily adjusting the spacing between first and second arms 110, 115 are also possible, as will be readily appreciated.

Figure 4:
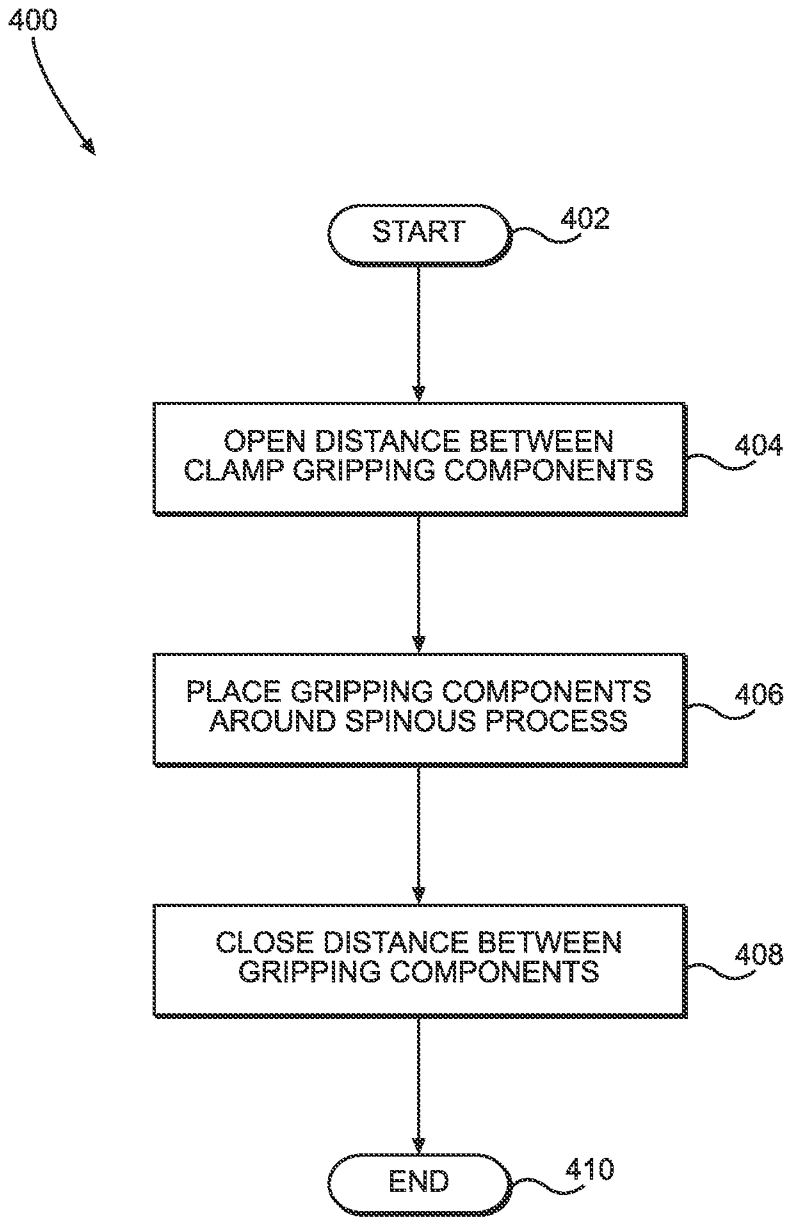
FIG. 4 illustrates a flowchart of an example summary method of attaching a spinous process clamp to a spinous process according to one embodiment of the present disclosure.

Moving next to FIG. 4, a flowchart of an example summary method of attaching a spinous process clamp to a spinous process is provided. Summary method 400 can represent one broad aspect of overall methods of use for a spinous process clamp, and it will be understood that various other steps, features, and details of such a broad aspect and overall methods of use are not provided here for purposes of simplicity. After a start step 402, a first process step 404 can involve opening or increasing a distance between gripping components of a spinous process clamp. This can involve rotating the thumbwheel of the clamp in a forward or clamp opening direction, for example. Step 404 can be manually or automatically performed, such as where a separate robotic system can be configured to operate a thumbwheel of the spinous process clamp.

At the following process step 406, the gripping components of the spinous process clamp can be placed around a spinous process of a patient. This can involve placing the gripping components and the overall spinous process clamp in such a way relative to the spinous process so as to facilitate a firm gripping or clamping onto the spinous process. Step 406 can be manually or automatically performed, such as where a separate robotic system can be configured to move and place the spinous process clamp.

The next process step 408 can involve closing or decreasing the distance between the gripping components. This can involve rotating the thumbwheel of the clamp in a reverse or clamp closing direction, for example. The distance between gripping components can be closed or decreased until they firmly grip the spinous process and affix the spinous process clamp in place relative to the patient. Step 408 can be manually or automatically performed, such as where a separate robotic system can be configured to operate a thumbwheel of the spinous process clamp. The method can then end at end step 410.

Figure 5A:
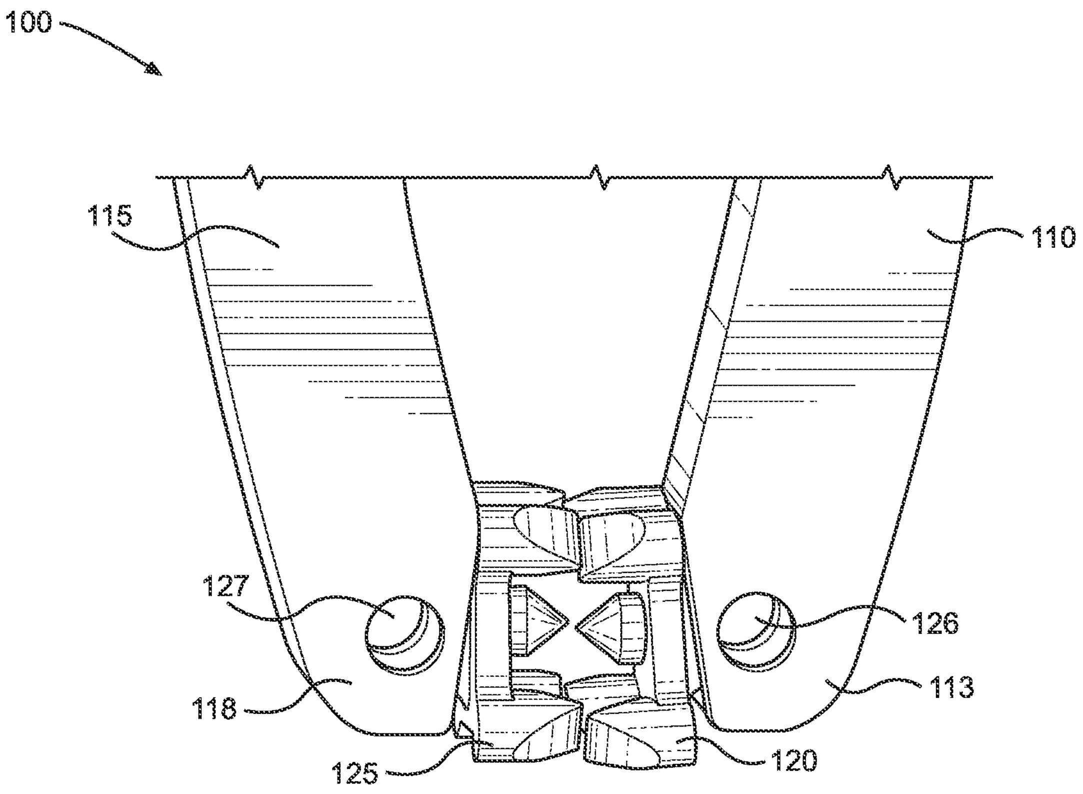
FIG. 5A illustrates in front elevation view an example pair of gripping components coupled to spinous process clamp arms according to one embodiment of the present disclosure.
Figure 5B:
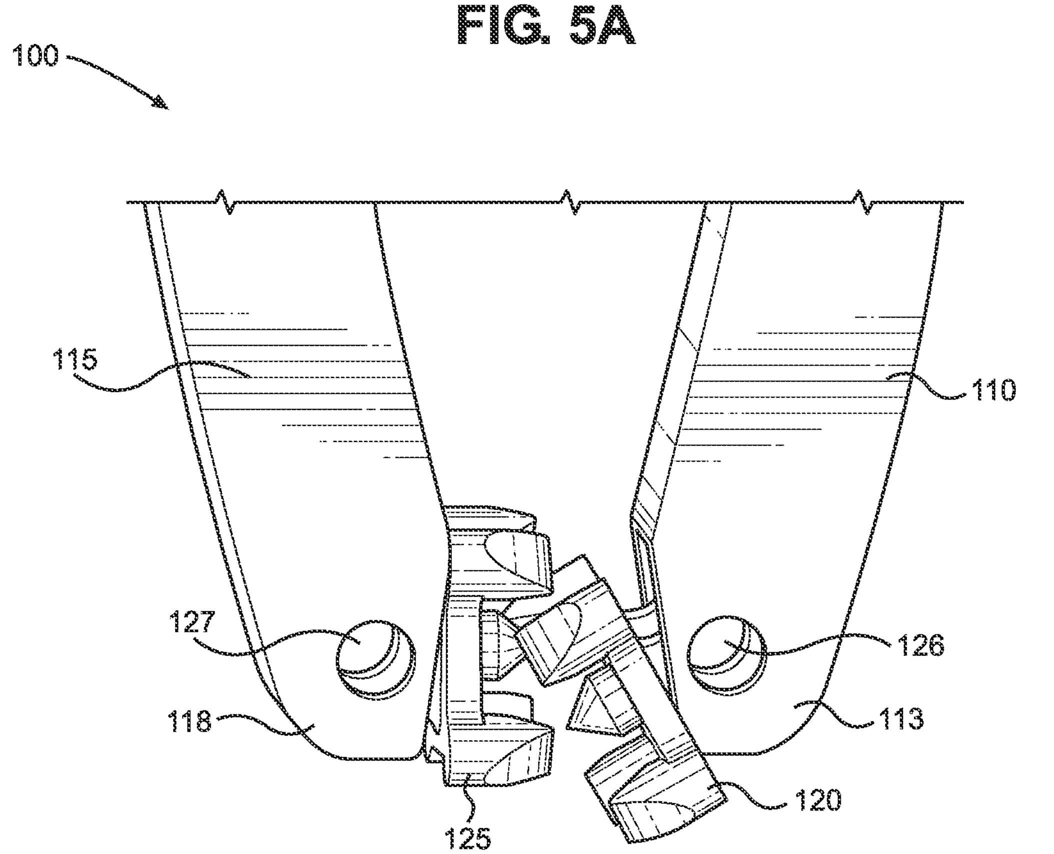
FIG. 5B illustrates in front elevation view the pair of gripping components of FIG. 5A at an alternative position according to one embodiment of the present disclosure.

Transitioning now to FIGS. 5A and 5B, an example pair of gripping components coupled to spinous process clamp arms are shown in front elevation views in one position and an alternative position respectively. First gripping component 120 can be coupled to first arm 110 at its bottom distal end 113, while second gripping component 125 can similarly be coupled to second arm 115 at its bottom distal end 118. In various arrangements, first and second gripping components 120, 125 can be identical or substantially similar. As shown, both first and second gripping components 120, 125 can be arranged such that they face each other so as to facilitate clamping onto and gripping of a spinous process that may be placed between them.

In some embodiments, one or both of first and second gripping components 120, 125 can be arranged to move relative its respective arm 110, 115, such as to facilitate better gripping and clamping on a given spinous process. For example, first gripping component 120 can be pivotally coupled to first arm 110 about an axis through first opening 126 in the first arm, while second gripping component 125 can be pivotally coupled to second arm 115 about an axis through second opening 127 in the second arm. This can be accomplished by way of pivot pins (not shown) inserted through first and second openings 126, 127 and portions of respective gripping components 120, 125, which pivot pins can function to hold the gripping components in place against respective first and second arms 110, 115 while also allowing the gripping components to pivot with respect to the arms. As shown, each of first and second gripping components 120, 125 can rotate about 10-15 degrees with respect to first and second arms 110, 115 respectively. Other ranges of motion are also possible, and it is also contemplated that one or both of first and second gripping components 120, 125 can have multiple axes of rotation with respect to first and second arms 110, 115 to facilitate further relative movement.

Figure 6A:
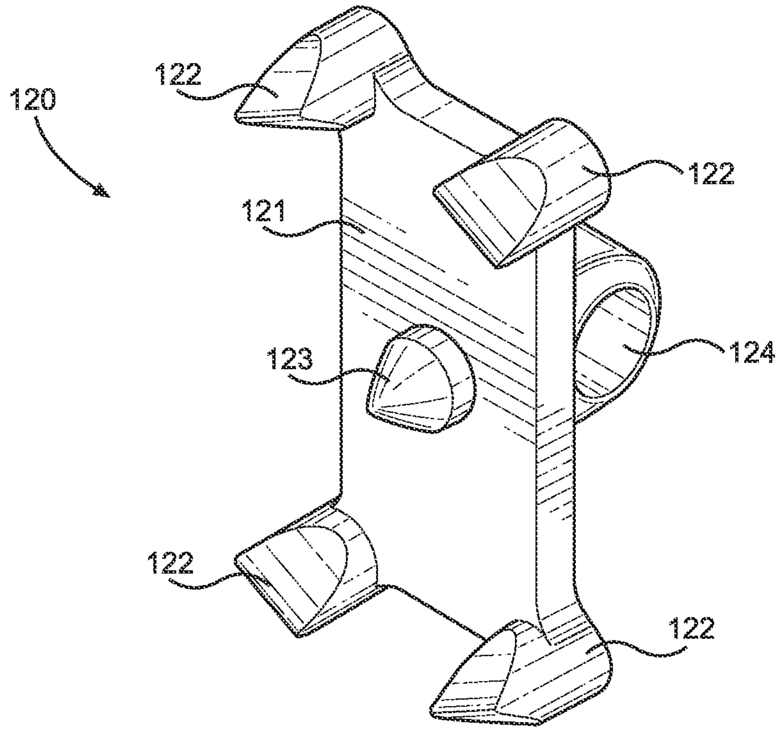
FIG. 6A illustrates in front perspective view an example gripping component for a spinous process clamp according to one embodiment of the present disclosure.
Figure 6B:
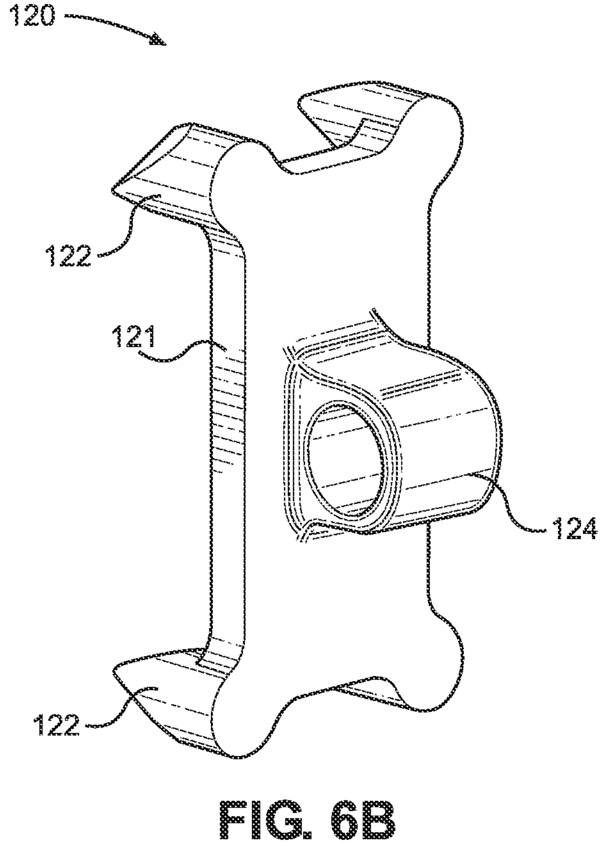
FIG. 6B illustrates in rear perspective view the gripping component of FIG. 6A according to one embodiment of the present disclosure.
Figure 6C:
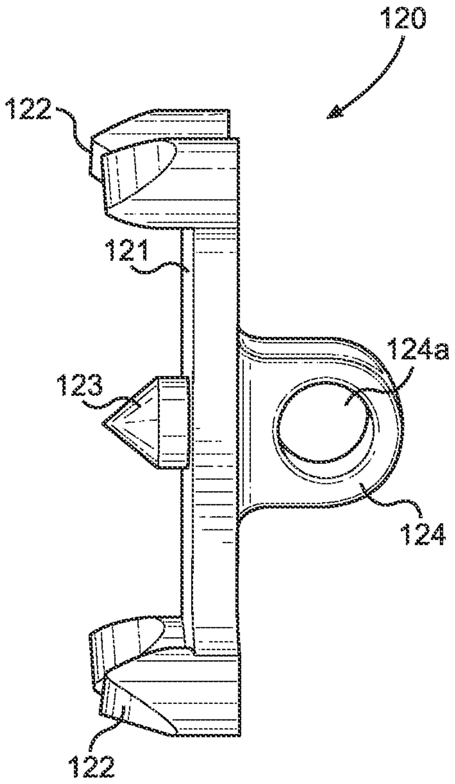
FIG. 6C illustrates in side elevation view the gripping component of FIG. 6A according to one embodiment of the present disclosure.

FIGS. 6A-6C illustrate an example gripping component for a spinous process clamp in front perspective, rear perspective, and side elevation views respectively. Again, gripping component 120 can be substantially similar or identical to gripping component 125 in the foregoing examples. Gripping component 120 can include a main body 121 defining an outer perimeter having a plurality of outer gripping teeth 122 distributed thereabout, as well as a central region having one or more central gripping teeth 123 extending therefrom. As shown, four outer gripping teeth 122 can extend from each corner of rectangular main body 121, while one central gripping tooth 123 can extend from the center of the main body. In various embodiments, gripping teeth 122, 123 can be about 4-5 mm wide and about 5-15 mm tall, although other dimensions are also possible.

As shown, gripping teeth 122, 123 can all extend in the same direction from main body 121 of gripping component 120, while pivot extension 124 can extend in the opposite direction from the main body. Pivot extension 124 can have an opening 124*a* therethrough to accommodate a pin inserted therethrough when the pivot extension is inserted into a slot at the bottom distal end of an arm of a spinous process clamp. For example, pivot extension 124 can be inserted into a slot at the interior of bottom distal end 113 of first arm 110 in the above example. A pivot pin (not shown) can then be inserted through both opening 124*a* in pivot extension 124 and opening 126 of first arm 110 to hold gripping component 120 in place against the first arm and also allow the gripping component to pivot with respect to the first arm. In some arrangement gripping component 120 can be integrally formed from machined surgical steel, although other compositions and materials may also be used.

Figure 7A:
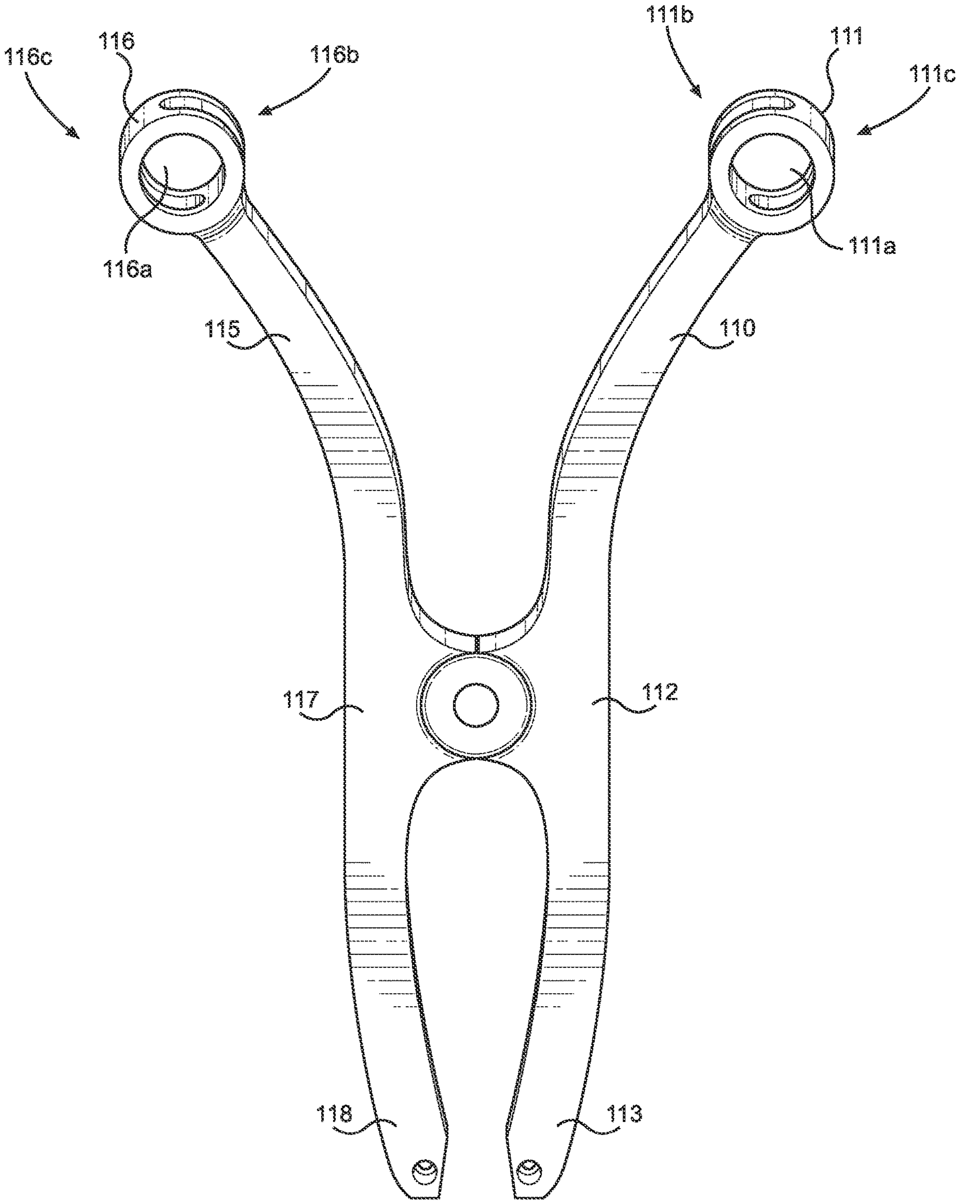
FIG. 7A illustrates in front elevation view an example pair of arms for a spinous process clamp according to one embodiment of the present disclosure.
Figure 7B:
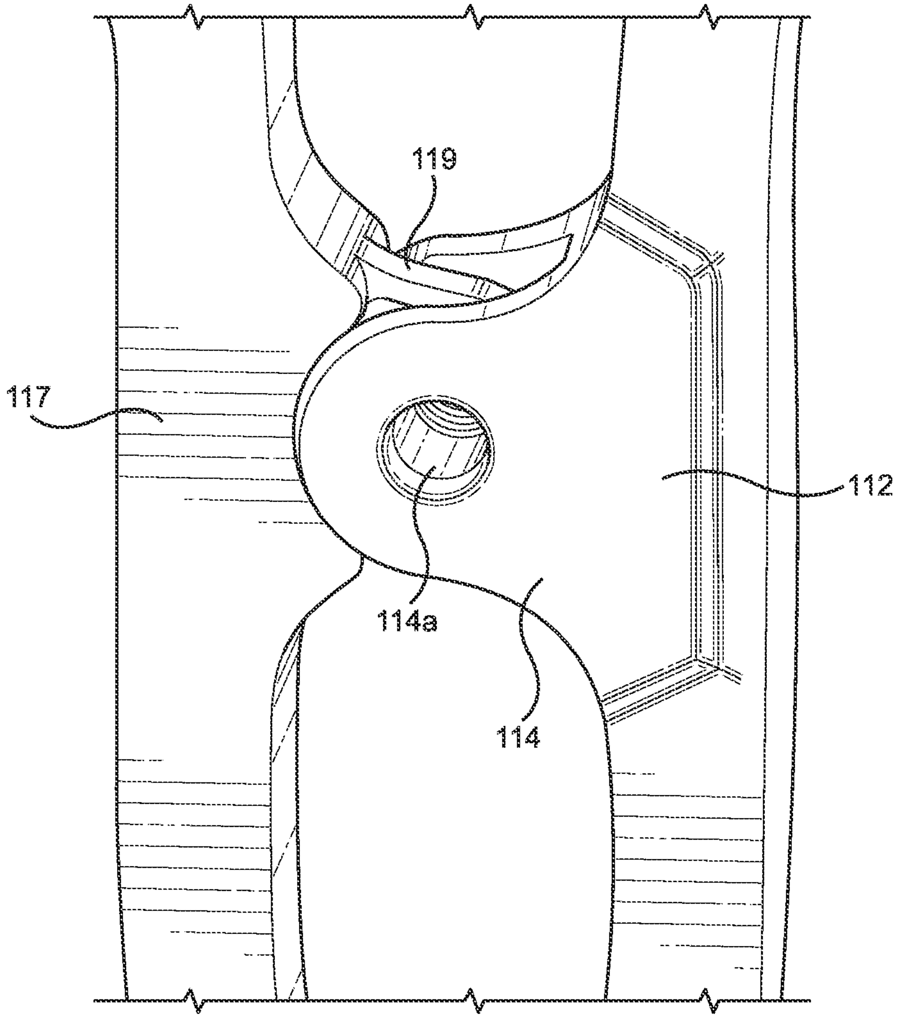
FIG. 7B illustrates in front elevation view an example coupling arrangement for the pair of arms of FIG. 7A according to one embodiment of the present disclosure.

FIG. 7A illustrates in front elevation view an example pair of arms for a spinous process clamp, while FIG. 7B illustrates in front elevation view an example coupling arrangement for this pair of arms. Again, first arm 110 can have a top distal end 111, a midsection 112, a bottom distal end 113, and a first pivoting feature 114, while second arm 115 can similarly have a top distal end 116, a midsection 117, a bottom distal end 118, and a second pivoting feature 119. Top distal ends 111, 116 of first and second arms 110, 115 can include hollow regions 111*a*, 116*a* configured to hold rotational bearings therein, as noted above. In addition, top distal ends 111, 116 can also include inside slots 111*b*, 116*b* at interior sidewalls thereof, as well as outside slots 111*c*, 116*c* at exterior sidewalls thereof. Inside slots 111*b*, 116*b* and outside slots 111*c*, 116*c* can be arranged to accommodate first and second threaded portions of a threaded bar passing therethrough respectively as the top distal ends 111, 116 move toward or away from each other along the threaded bar when first and second arms 110, 115 pivot.

As noted above, midsection 117 of second arm 115 can be pivotally coupled to midsection 112 of first arm 110 by way of a pivoting arrangement between a first pivoting feature 114 of the first arm and a second pivoting features 119 of the second arm. In some arrangements, second pivoting feature 119 can extend inward from second arm 115 and fit between multiple portions of first pivoting feature 114 that extend inward from first arm 110. Each of these portions of first pivoting feature 114 can have an opening 114*a* therethrough to facilitate the insertion of a pivot pin (not shown), and second pivoting feature 119 can also have an opening (not shown) therethrough to facilitate insertion of the pivot pin. Use of such a pivot pin can function to hold first and second arms 110, 115 in place against each other while also allowing the arms to pivot with respect to each other about the pin.

Figure 8A:
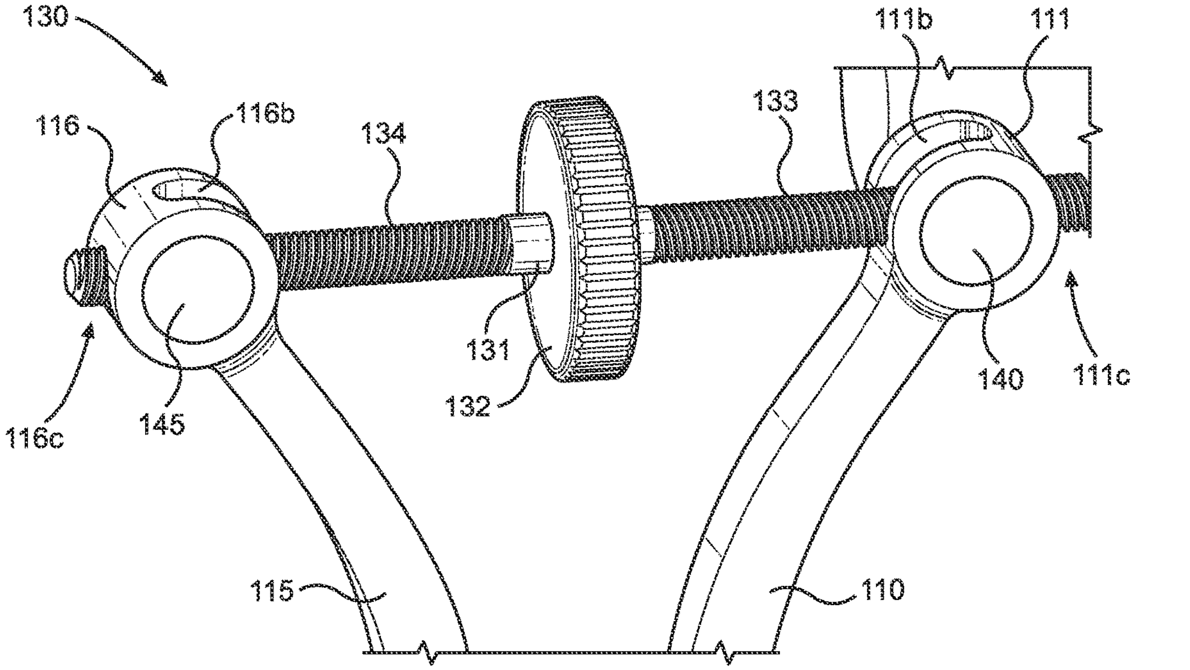
FIG. 8A illustrates in front perspective view an example adjustable spacing arrangement for a spinous process clamp according to one embodiment of the present disclosure.
Figure 8B:
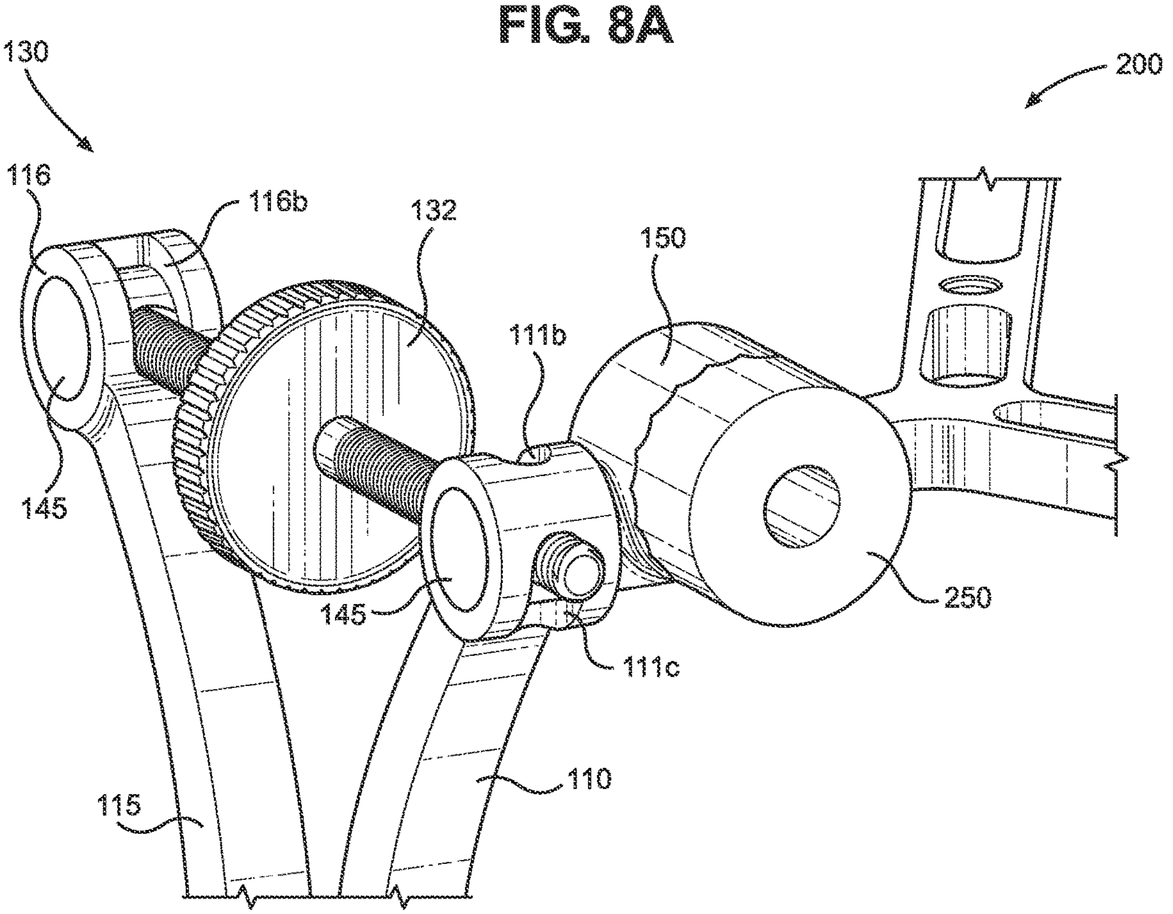
FIG. 8B illustrates in side perspective view the adjustable spacing arrangement of FIG. 8A according to one embodiment of the present disclosure.

Referring next to FIGS. 8A and 8B, an example adjustable spacing arrangement for a spinous process clamp is shown in front perspective and side perspective views respectively. As noted above, adjustable spacing arrangement 130 can include threaded bar 131, thumbwheel 132 located proximate the center of the threaded bar, first and second threaded portions 133, 134 of the threaded bar, and first and second receiving bearings 140, 145 located on opposite sides of the thumbwheel toward the distal ends of the threaded bar. First and second receiving bearings 140, 145 can be located at and rotatable within top distal ends 111, 116 of first and second arms 110, 115 respectively. Inside slots 111*b*, 116*b* and outside slots 111*c*, 116*c* in top distal ends 111, 116 of first and second arms 110, 115 can be arranged to accommodate first and second threaded portions 133, 134 of threaded bar 131 passing therethrough respectively as the top distal ends move toward or away from each other along the threaded bar.

In some arrangements, threaded bar 131 can be a two-way custom screw with right-hand and left-hand threads on either side of thumbwheel 132. For example, first threaded portion 133 can have a right-hand thread while second threaded portion 134 can have a left-hand thread. Accordingly, a threaded internal opening of first receiving bearing 140 can be configured to receive the right-hand thread of first threaded portion 133, while a threaded internal opening of second receiving bearing 145 can be configured to receive the left-hand thread of second threaded portion 134. In various embodiments, the pitch of each thread can be about 1.5 mm, although other pitches can also be used.

Rotation of thumbwheel 132 in a forward direction can result in rotating threaded bar 131 and its first and second threaded portions 133, 134 in a forward direction, which in turn moves the first and second receiving bearings 140, 145 inward along the threaded bar toward the thumbwheel. Similarly, rotation of thumbwheel 132 in a reverse direction can result in rotating threaded bar 131 and its first and second threaded portions 133, 134 in a reverse direction, which in turn moves the first and second receiving bearings 140, 145 outward along the threaded bar away from the thumbwheel. In either directional motion the receiving bearing 140, 145 can both move equally, such that top distal ends 111, 116 of first and second arms 110, 115 both move equally as well.

Figure 9:
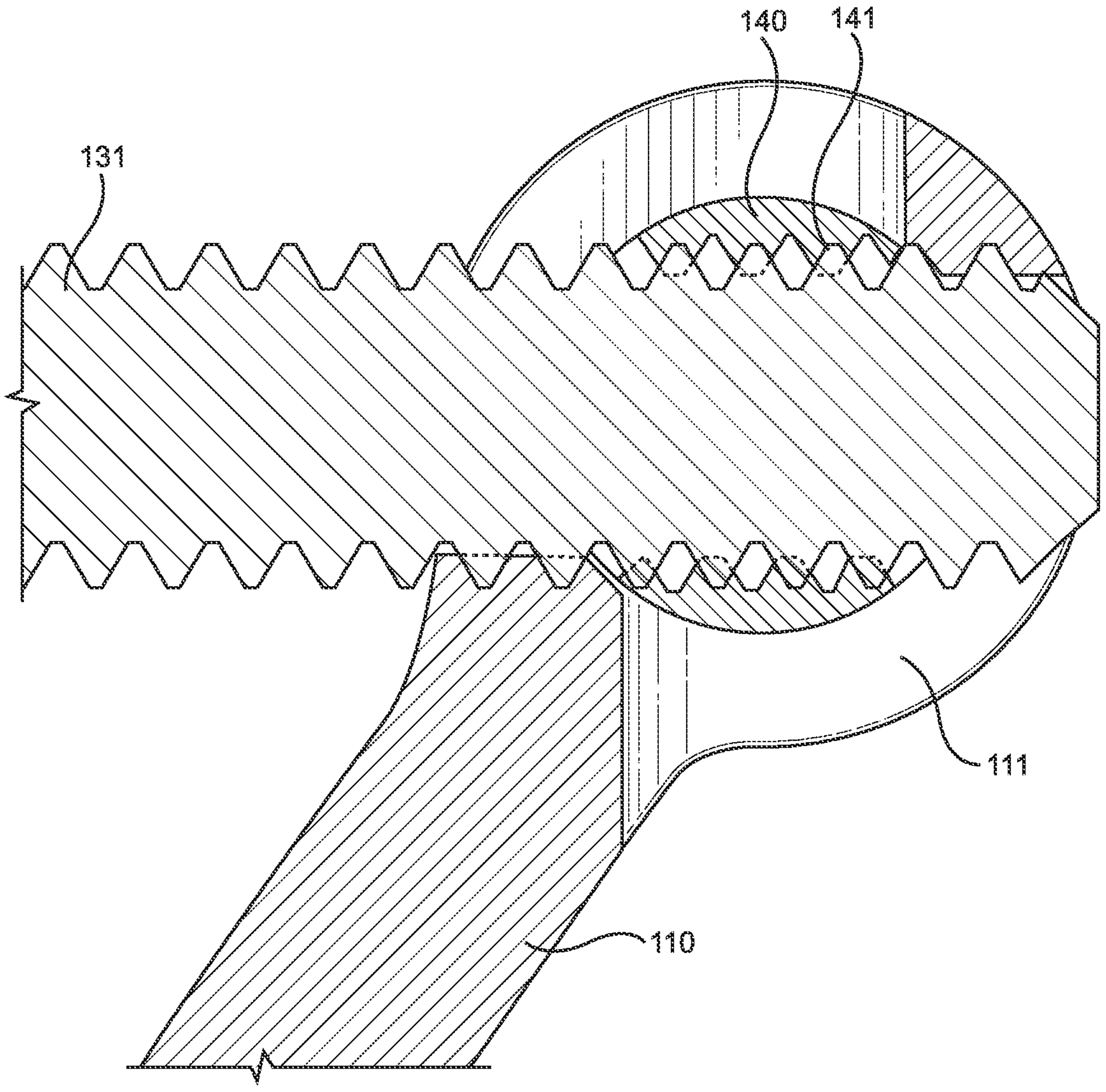
FIG. 9 illustrates in front perspective view an example receiving bearing for a spinous process clamp according to one embodiment of the present disclosure.

Continuing with FIG. 9 an example receiving bearing within a spinous process clamp is shown in front cross-section view. Receiving bearing 140 can be identical or substantially similar to receiving bearing 145 noted above and can be cylindrically shaped and sized to fit snugly within a suitably sized cylindrically shaped hollow region within top distal end 111 of an arm 110 of the spinous process clamp. Receiving bearing 140 can then rotate within this hollow region within top distal end 111, since the relative orientation of the top distal end will rotate with respect to the receiving bearing as the top distal end and receiving bearing move together back and forth along threaded bar 131. To facilitate such movement, receiving bearing 140 can have a central opening extending longitudinally therethrough, and this central opening can have an internal threaded portion 141 configured to receive and mate with the threaded bar.

Figure 10A:
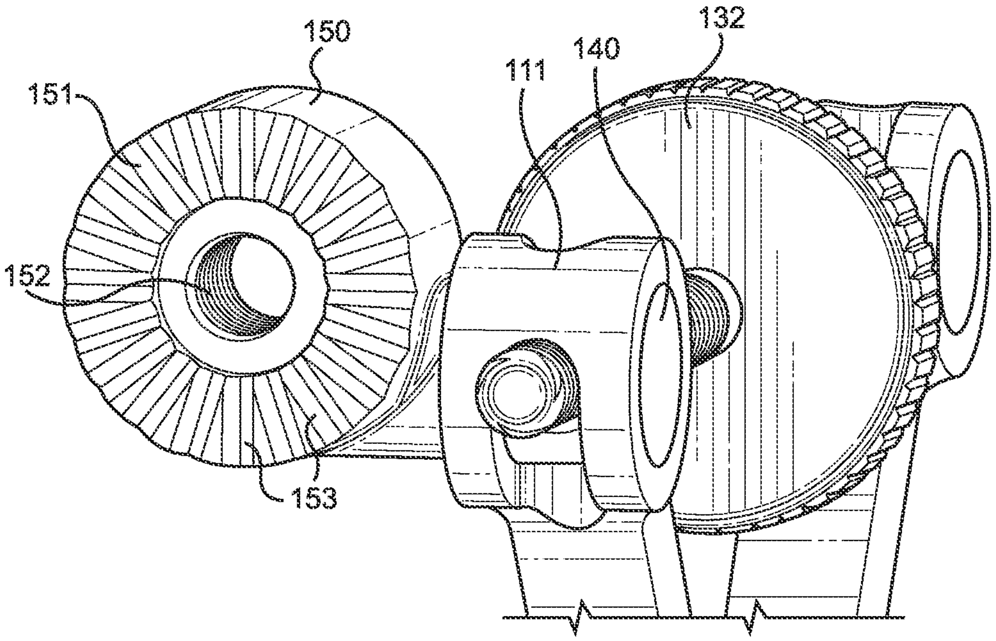
FIG. 10A illustrates in side perspective view an example clamp coupling component for a spinous process clamp according to one embodiment of the present disclosure.
Figure 10B:
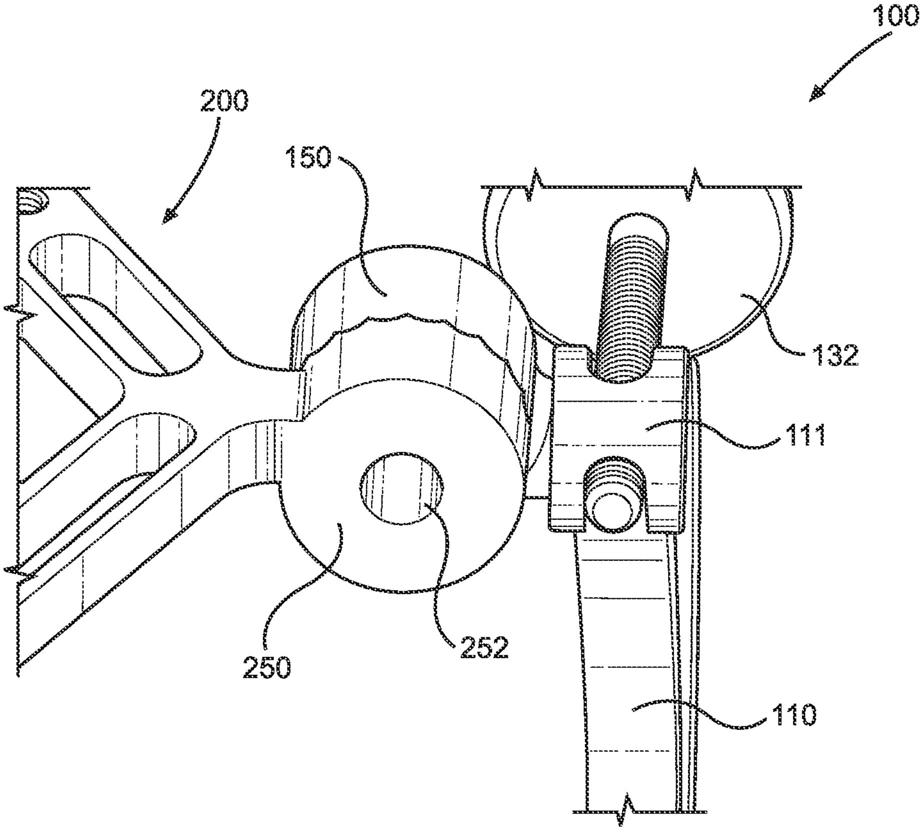
FIG. 10B illustrates in top perspective view the clamp coupling component of FIG. 10A rotationally coupled to a positioner coupling component for a surgical fiducial marker positioner according to one embodiment of the present disclosure.

FIG. 10A illustrates in side perspective view an example clamp coupling component for a spinous process clamp, while FIG. 10B illustrates in top perspective view the clamp coupling component of FIG. 10A rotationally coupled to a positioner coupling component for a surgical fiducial marker positioner. As noted above, clamp coupling component 150 can be attached or otherwise coupled to top distal end 111 of first arm 110, among other possible locations at spinous process clamp 100. Clamp coupling component 150 can define a cylindrical shape having a vertically oriented circular mating face 151 and a threaded central opening 152 extending at least partially therethrough. Mating face 151 can have a plurality of ridges 153 that can be arranged in an axial pattern for mating with a similar axial pattern of ridges on a mating face of positioner coupling component 250. In addition to having a corresponding mating face that is configured to mate and operate with mating face 151, positioner coupling component 250 can similarly have a threaded central opening 252 arranged to align with the threaded central opening 152 of clamp coupling component 150 when both mating faces are engaged.

In various arrangements, clamp coupling component 150 can be affixed to and can be stationary with spinous process clamp 100, while positioner coupling component 250 can be configured to rotate with respect to the clamp coupling component. Rotation can be about a horizontal axis that extends through the centers of threaded central openings 152 and 252, such that the position of entire surgical fiducial marker positioner 200 is rotated about this axis. As will be readily appreciated, rotation of positioner coupling component 250 with respect to a stationary clamp coupling component 150 can result in the relative rotation of its mating face with mating face 151 of the clamp coupling component.

Ridges 153 on mating face 151 can fit snugly between corresponding ridges on the mating face of rotating positioner coupling component 250, such that multiple discrete rotational orientations can be achieved. For example, where clamp coupling component 150 has a mating face 151 with ten axially arranged ridges 153, then positioner coupling component 250 can have a matching mating face with ten similarly axially arranged ridges, and this can facilitate at least ten different discrete rotational positions of surgical fiducial marker positioner 200 with respect to the spinous process clamp 100. Of course, more or fewer axially arranged ridges are also possible, and clamp coupling component 150 as shown can have twenty such axially arranged ridges 153 for twenty different discrete rotational positions in this particular illustrative example.

In some embodiments, a thumbscrew, wing nut, or other coupling arrangement (not shown) can be used within threaded internal openings 151, 251 to loosen and tighten positioner coupling component 250 with respect to clamp coupling component 150. One possible such coupling arrangement can involve the thumbwheel and pin arrangement 154 shown in FIG. 2B above, which can involve a threaded pin inserted into threaded central openings 252 and 152 to tighten positioner coupling component 250 against clamp coupling component 150. As will be readily appreciated, loosening such a coupling arrangement can allow for the ready rotational adjustment of surgical fiducial marker positioner 200 with respect to spinous process clamp 100, while tightening such a coupling arrangement can result in affixing or setting a discrete rotational position of the surgical fiducial marker positioner with respect to the spinous process clamp.

While clamp coupling component 150 and positioner coupling component 250 are shown as being vertically oriented with respect to spinous process clamp 100 in FIGS. 10A-B and other illustrative examples herein, it will be readily appreciated that these coupling components can be oriented horizontally or otherwise, such that relative rotation can be about a differently oriented axis. It is also contemplated that more than one rotational axis can be used for adjusting the positioning of surgical fiducial marker positioner 200 in some embodiments. For example, a secondary mating coupling component arrangement can allow for rotation of the surgical fiducial marker positioner 200 with respect to the spinous process clamp 100 about a vertical axis as well as a horizontal axis.

Figure 11:
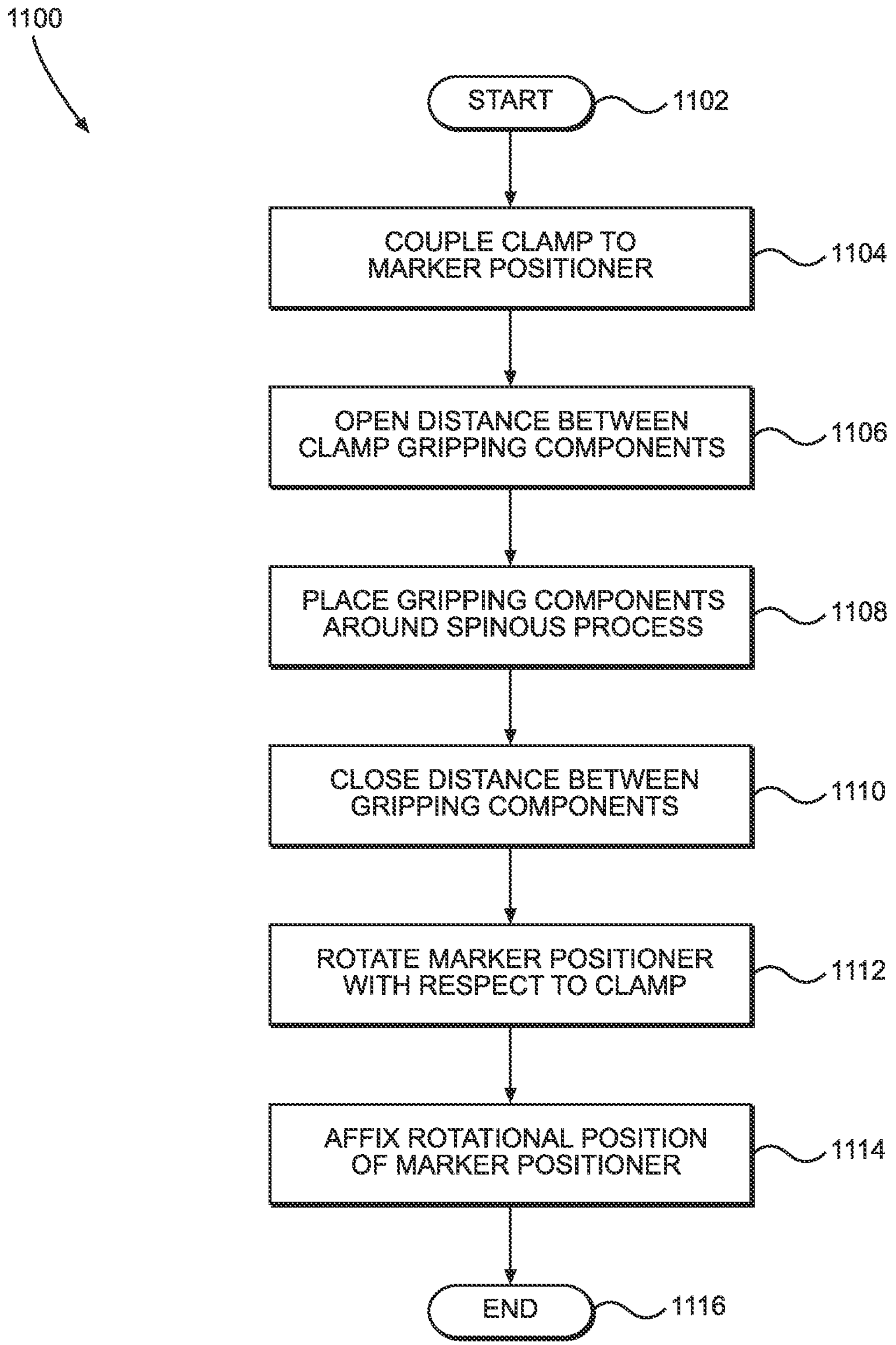
FIG. 11 illustrates a flowchart of an example detailed method of using a spinous process clamp according to one embodiment of the present disclosure.

Lastly, FIG. 11 provides a flowchart of an example detailed method 1100 of using a spinous process clamp. Detailed method 1100 can represent one possible way of using a spinous process clamp, and it will be understood that various other steps, features, and details of such a detailed method are not provided here for purposes of simplicity. After a start step 1102, a first process step 1104 can involve coupling a spinous process clamp to a surgical fiducial marker positioner. This can be a rotational coupling, such as that which is set forth above. Step 1102 can be manually or automatically performed, such as where a separate robotic system can be configured to couple a spinous process clamp to a surgical fiducial marker positioner.

At a following process step 1106, a distance between gripping components of a spinous process clamp can be opened or increased. This can involve rotating a thumbwheel of the clamp in a forward or clamp opening direction, for example. Step 1106 can be manually or automatically performed, such as where a separate robotic system can be configured to operate a thumbwheel of the spinous process clamp.

At subsequent process step 1108, the gripping components of the spinous process clamp can be placed around a spinous process of a patient. This can involve placing the gripping components and the overall spinous process clamp in such a way relative to the spinous process so as to facilitate a firm gripping or clamping onto the spinous process. Step 1108 can be manually or automatically performed, such as where a separate robotic system can be configured to move and place the spinous process clamp.

The next process step 1110 can involve closing or decreasing the distance between the gripping components. This can involve rotating the thumbwheel of the clamp in a reverse or clamp closing direction, for example. The distance between gripping components can be closed or decreased until they firmly grip the spinous process and affix the spinous process clamp in place relative to the patient. Step 1110 can be manually or automatically performed, such as where a separate robotic system can be configured to operate a thumbwheel of the spinous process clamp.

At a following process step 1112, the surgical fiducial marker positioner can be rotated with respect to the spinous process clamp. This can be done while the spinous process clamp is coupled to the surgical fiducial marker positioner and the spinous process clamp is affixed in place relative to the patient. Also, this can involve loosening any couplings or other attachments between these items and then rotating or swiveling the surgical fiducial marker positioner about an axis through the couplings, for example. Such couplings can be a clamp coupling component and a positioner coupling component as detailed above. Step 1112 can be manually or automatically performed, such as where a separate robotic system can be configured to rotate the surgical fiducial marker positioner relative to the spinous process clamp.

Subsequent process step 1114 can involve affixing the rotational position of the surgical fiducial marker positioner relative to the spinous process clamp. This can involve the use of thumbscrew or wing nut, for example, which can be tightened on a clamp coupling component as noted above. Step 1114 can be manually or automatically performed, such as where a separate robotic system can be configured to affix the surgical fiducial marker positioner in place to the spinous process clamp. The method can then end at end step 1116.

For foregoing method 1100, it will be appreciated that not all process steps are necessary, and that other process steps may be added in some arrangements. For example, changing the clamp from one spinous process to another might take place in some arrangements. Furthermore, the order of steps may be altered in some cases, and some steps may be performed simultaneously. For example, step 1104 may be performed later in the process in some cases. Although known process steps are provided for the various techniques in method 1100, it will be appreciated that any other suitable similar method for using a spinous process clamp can also be used. Other variations and extrapolations of the disclosed methods will also be readily appreciated by those of skill in the art.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A spinous process clamp, comprising:

a first arm having a top distal end, a midsection, and a bottom distal end;

a first gripping component located proximate the bottom distal end of the first arm and configured to grip a side of a spinous process of a patient;

a second arm positioned opposite the first arm and having a top distal end, a midsection, and a bottom distal end, wherein the midsection of the second arm is pivotally coupled to the midsection of the first arm;

a second gripping component located proximate the bottom distal end of the second arm and configured to grip a side of the spinous process opposite the side gripped by the first gripping component, wherein pivoting the first and second arms with respect to each other adjusts a distance between the first and second gripping components;

an adjustable spacing arrangement having a threaded bar configured to rotate about a first axis of rotation, a first receiving bearing located within and configured to rotate relative to the top distal end of the first arm, and a second receiving bearing located within and configured to rotate relative to the top distal end of the second arm, wherein the adjustable spacing arrangement is configured to maintain a pivoted position of the first and second arms with respect to each other, and wherein adjustment of the adjustable spacing arrangement results in pivoting the first and second arms with respect to each other; and a coupling component coupled to the first arm proximate the first receiving bearing and extending laterally from the first arm in a direction that is orthogonal to the first axis of rotation, wherein the coupling component is configured to rotationally couple the spinous process clamp to a separate surgical component about a second axis of rotation that is proximate and substantially parallel to the first axis of rotation.

2. The spinous process clamp of claim 1, wherein the coupling component is configured to facilitate at least ten different discrete rotational positions of the separate surgical component with respect to the spinous process clamp.

3. The spinous process clamp of claim 1, wherein the separate surgical component is a surgical fiducial marker positioner.

4. The spinous process clamp of claim 3, wherein fiducial markers of the surgical fiducial marker positioner include infrared reflective balls.

5. The spinous process clamp of claim 1, wherein the adjustable spacing arrangement further includes a thumbwheel located on the threaded bar.

6. The spinous process clamp of claim 5, wherein rotation of the thumbwheel in a forward direction causes the top distal ends of both arms to move toward the thumbwheel equally and rotation of the thumbwheel in a reverse direction causes the top distal ends of both arms to move away from the thumbwheel equally.

7. The spinous process clamp of claim 5, wherein the threaded bar includes a left-hand thread on one side of the threaded bar and a right-hand thread on the opposite side of the threaded bar.

8. The spinous process clamp of claim 1, wherein each of the first and second receiving bearings include a threaded interior passage configured to receive the threaded bar.

9. The spinous process clamp of claim 1, wherein each of the first gripping component and the second gripping component defines an outer perimeter having a plurality of gripping teeth distributed thereabout.

10. The spinous process clamp of claim 9, wherein each of the first gripping component and the second gripping component further includes at least one gripping tooth located within the outer perimeter.

11. The spinous process clamp of claim 1, wherein the first gripping component is pivotally coupled to the bottom distal end of the first arm.

12. The spinous process clamp of claim 1, wherein the coupling component is configured to facilitate multiple different discrete rotational positions of the separate surgical component with at least one of the discrete rotational positions locating the separate surgical component above the threaded bar and at least one other of the discrete rotational positions locating the separate surgical component below the threaded bar.

13. The spinous process clamp of claim 1, wherein the first arm, second arm, and threaded bar combine to define a plane, and wherein the coupling component extends laterally from the first arm in a direction that is perpendicular to the plane.

14. The spinous process clamp of claim 13, wherein the plane extends in a vertical direction, the first axis of rotation extends in a horizontal direction within the plane, and the second axis of rotation extends through the coupling component in a horizontal direction parallel to the plane.

15. The spinous process clamp of claim 1, wherein the distance between the coupling component and the first receiving bearing is less than a diameter of the coupling component.

16. The spinous process clamp of claim 1, wherein the coupling component defines a cylindrical shape having a vertically oriented circular mating face having a plurality of ridges arranged in an axial pattern and a threaded central opening extending therethrough along the second axis of rotation and configured to receive a threaded thumbscrew therein.

17. A surgical fiducial marker system, comprising:

a spinous process clamp configured to grip a spinous process of a patient, wherein the spinous process clamp includes a first arm having a top distal end, a midsection, and a bottom distal end, a second arm having a top distal end, a midsection, and a bottom distal end, the second arm pivotally coupled to the first arm, an adjustable spacing arrangement having a threaded bar configured to rotate about a first axis of rotation, a first receiving bearing located within and configured to rotate relative to a top distal end of the first arm, a second receiving bearing located within and configured to rotate relative to a top distal end of the second arm, and a clamp coupling component coupled to the first arm proximate the first receiving bearing and extending laterally from the first arm in a direction that is orthogonal to the first axis of rotation; and a surgical fiducial marker positioner rotationally coupled to the clamp coupling component about a second axis of rotation that is proximate and substantially parallel to the first axis of rotation, wherein the surgical fiducial marker positioner is configured to position a plurality of surgical fiducial markers into a fixed arrangement relative to the patient while the spinous process clamp grips the spinous process of the patient.

18. The surgical fiducial marker system of claim 17, wherein the spinous process clamp further includes:

a first gripping component located proximate the bottom distal end of the first arm and configured to grip a side of the spinous process of the patient; and a second gripping component located proximate the bottom distal end of the second arm and configured to grip a side of the spinous process opposite the side gripped by the first gripping component, wherein pivoting the first and second arms with respect to each other adjusts a distance between the first and second gripping components.

19. The surgical fiducial marker system of claim 17, wherein the clamp coupling component is configured to facilitate at least ten different discrete rotational positions of the surgical fiducial marker positioner with respect to the spinous process clamp.

20. The surgical fiducial marker system of claim 17, wherein the clamp coupling component rotationally mates with a corresponding positioner coupling component on the surgical fiducial marker positioner.

21. The surgical fiducial marker system of claim 20, wherein the clamp coupling component and positioner coupling component are configured to facilitate multiple different discrete rotational positions of the surgical fiducial marker positioner with at least one of the discrete rotational positions locating all of the surgical fiducial markers at positions above the threaded bar and at least one other of the discrete rotational positions locating all of the surgical fiducial markers at positions below the threaded bar.

* * * * *